United States Patent [19]

Minekane et al.

[11] Patent Number: 4,664,885
[45] Date of Patent: May 12, 1987

[54] AUTOMATIC CHEMICAL ANALYZER

[75] Inventors: Tomiharu Minekane; Kouji Matsumoto, both of Ootawara, Japan

[73] Assignee: Tokyo Shibaura Denki Kabushiki Kaisha, Kawasaki, Japan

[21] Appl. No.: 684,159

[22] Filed: Dec. 20, 1984

Related U.S. Application Data

[63] Continuation of Ser. No. 396,369, Jul. 8, 1982, abandoned.

[30] Foreign Application Priority Data

Jul. 13, 1981 [JP] Japan ................. 56-109857

[51] Int. Cl.⁴ .................... G01N 35/04; G01N 35/06
[52] U.S. Cl. ........................... 422/65; 422/63; 422/67; 436/47; 436/179
[58] Field of Search ............. 422/63, 65, 67; 436/47, 436/48, 49, 179

[56] References Cited

U.S. PATENT DOCUMENTS

| | | | |
|---|---|---|---|
| 3,193,358 | 7/1965 | Baruch | 422/67 X |
| 3,489,525 | 1/1970 | Natelson | 422/67 X |
| 3,762,879 | 10/1973 | Moran | 422/67 X |
| 3,869,252 | 3/1975 | Haug | 422/65 |
| 3,883,305 | 5/1975 | Hoskins et al. | 422/67 X |
| 4,158,545 | 6/1979 | Yamashita et al. | 436/47 |
| 4,224,278 | 9/1980 | Hogen Esch | 422/65 |
| 4,322,216 | 3/1982 | Lillig et al. | 422/67 X |
| 4,363,782 | 12/1982 | Yamashita | 422/67 X |
| 4,366,119 | 12/1982 | Takeuchi | 422/67 X |

FOREIGN PATENT DOCUMENTS 2607055  9/1977  Fed. Rep. of Germany .

Primary Examiner—David L. Lacey
Assistant Examiner—Robert J. Hill, Jr.
Attorney, Agent, or Firm—Cushman, Darby & Cushman

[57] ABSTRACT

An automatic chemical analyzer which comprises a reaction line system including a plurality of reaction lines each consisting of a plurality of reaction tubes arranged in a row, means for distributing samples to the reaction tubes, and means for carrying out chemical analysis of samples contained in the reaction tubes. The reaction line system is provided with a driving mechanism for driving the individual reaction lines intermittently and independently of one another, and is constructed to sure that the feed rate of the individual reaction lines can be freely changed. The automatic chemical analyzer can thus be reduced in size and nevertheless can quickly and reliably make analysis of a number of samples for a number of items.

7 Claims, 12 Drawing Figures

AUTOMATIC CHEMICAL ANALYZER

This is a continuation of application Ser. No. 396,369, filed July 8, 1982, now abandoned.

BACKGROUND OF THE INVENTION

This invention relates to automatic chemical analyzers and, more particularly, to an automatic chemical analyzer in which a plurality of reaction lines are driven independently to permit chemical analysis of samples for a large number of analysis items in a short period of time.

Recently, the importance of the examination for disease diagnosis has been increasing, and also the cases and items of examination are both increasing. In order to cope with this, an automatic examination system has been desired in laboratories.

An automatic chemical analyzer provides results of analysis which are used as the important reference for diagnosis and are thus deeply related to the patient's life. To improve such automatic chemical analyzer, which is used in a hospital or like place where limited personnel and space are available, therefore, the following considerations must be paid.

(1) The quantity of sample to be extracted from the patient's body must very small lest pain should be given to the patient. Also, the quantity of a reagent to be added to the extracted sample should be very small so that the cost of analysis may be low.

(2) A number of different samples can be quickly analyzed to obtain results of analysis.

(3) The analyzer must be conveniently used so that a number of samples may be analyzed for a number of items by a limited number of personnel.

(4) The analyzer must reliably provide accurate results of analysis which are important diagnosis data concerned with the patient's life.

(5) The analyzer may be small in size so that it requires a small space.

These improvements have been remarkably achieved with prior art automatic chemical analyzers. However, because of the necessity to quickly analyze a number of different samples for a number of different items, a great number of reaction tubes to contain samples and also a great number of measuring sections are required. Therefore, there is a trend for greater size of equipment despite the demand for smaller size.

In the usual automatic chemical analyzer, a single reaction line consisting of a plurality of reaction tubes arranged in a row is provided for a single analysis item. That is, where analysis is made for 16 items, for instance, 16 reaction lines are provided. In this system, in which an equal number of reaction lines to the number of necessary analysis items are provided, the number of reaction lines is limited by the size of the equipment from the following grounds.

Figure 1:
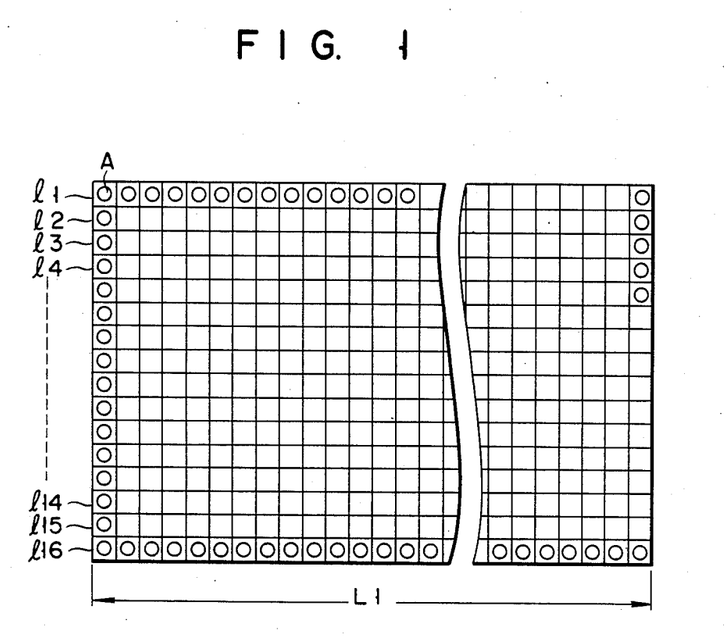
FIG. 1 is a pictorial plan view showing the arrangement of reaction lines in a prior art automatic chemical analyzer.

The length of the reaction line is dependent upon the reaction time and treatment speed. Consider now a system which has 16 reaction lines $l_1$ to $l_{16}$ each consisting of a plurality of reaction tubes A arranged in a row, as shown in FIG. 1. Suppose the interval of the reaction tubes in the same reaction line to be 25 mm, the reaction time to be 15 minutes and the treatment speed to be 90 samples per hour. Then the running speed of the reaction line is 40 seconds per sample, for the treatment speed is 90 samples per hour. The reaction time of 15 minutes means that 22.5 samples are continually on the reaction line during this time interval. This means that the length $L_1$ of the reaction line must be at least $25 \times 22.5 = 562.5$ mm. Therefore, if it is intended to double or triple the treatment speed without reducing the reaction time, the length $L_1$ of the reaction line has to be doubled or tripled, which is impractical. The reaction time must be at least 10 minutes from the clinical requirements although it varies with the analysis items. In addition, the number of reaction lines must increase with increasing number of analysis items. In consequence, to permit quick analysis for a great number of items very large size equipment is necessary. Furthermore, in the usual automatic chemical analyzer each reaction line is designed for an analysis item, which requires the longest reaction time from the clinical standpoint. Waste time, therefore, is inevitable with the reaction lines which are provided for analysis items requiring shorter reaction time periods, which is undesired from the standpoint of the quick analysis.

SUMMARY OF THE INVENTION

An object of the invention is to provide an automatic chemical analyzer, which permits quick and reliable treatment of a number of samples for a number of items.

According to the invention, there is provided an automatic chemical analyzer, which comprises a reaction line system including a plurality of reaction lines each consisting of a plurality of reaction tubes arranged in a row, means for distributing samples to reaction tubes and means for effecting chemical analysis of the samples in the reaction tubes, the reaction system being provided with a driving mechanism for intermittently driving the individual reaction lines independently of one another.

DETAILED DESCRIPTION OF THE PREFERRED EMBODIMENT

Now, an embodiment of the invention will be described with reference to the drawings.

Figure 2:
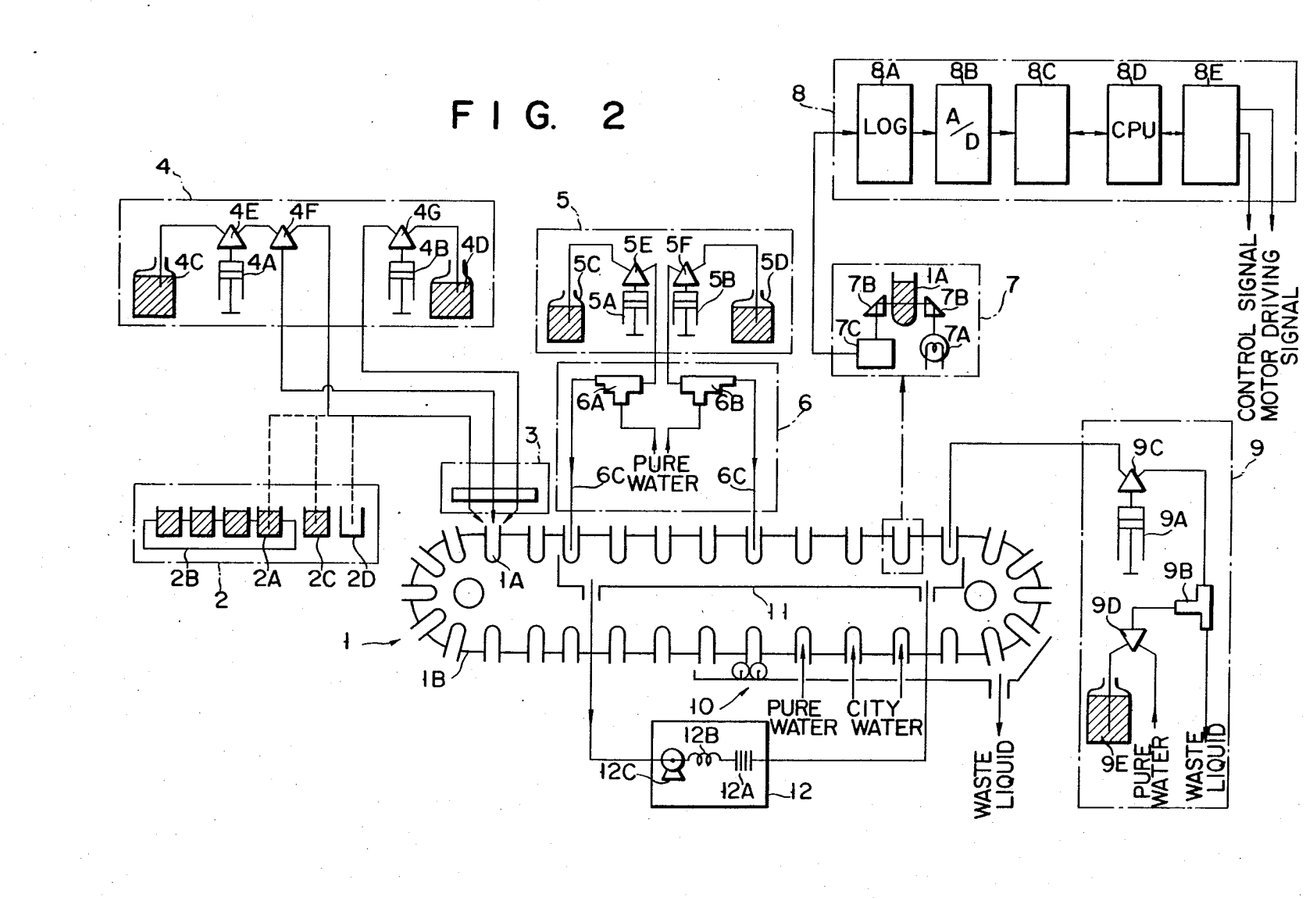
FIG. 2 is a system block diagram showing one embodiment of the automatic chemical analyzer according to the invention.

FIG. 2 is a system block diagram showing one embodiment of the automatic chemical analyzer according to the invention. This automatic chemical analyzer comprises a reaction line system 1, a sample container section 2, a sampling mechanism 3, a sampling control section 4, a reagent dispensing control section 5, a reagent dispensing mechanism 6, a photometry section 7, a discharge section 9, a control system 8, a cleaning section 10, a constant temperature bath 11, and a constant temperature control section 12. The reaction line system 1 includes a plurality of endless chain conveyers 1B, each of which conveys a plurality of reaction tubes 1A arranged in rows. The sample container section 2 includes a plurality of sample containers 2A to contain samples, a sample container holder 2B which holds the sample containers 2A, a standard serum container 2C to contain a standard serum, and a cleaning pool 2D in which nozzles to be described later are cleaned. The sampling mechanism 3 includes a plurality of nozzles and a mechanism for moving these nozzles. Samples and dilution water are poured from these nozzles into reaction tubes 1A. The sampling control section 4 includes dispensing syringes 4A, dilution syringes 4B, a pure water container 4C, a dilution water container 4D and electromagnetic valves 4E to 4G. The reagent dispensing control section 5 includes reagent dispensing syringes 5A and 5B, a first reagent container 5C, a second reagent container 5D and electromagnetic valves 5E and 5F. The reagent dispensing mechanism 6 includes three-way valves 6A and 6B, which serve to switch a pure water path and a reagent path, and reagent dispensing nozzles 6C. The photometric section 7 includes light sources 7A, prisms 7B and photometers 7C. Light from each light source 7A is led along a light path provided by the associated prisms 7B. At this time, it is transmitted through the reaction tube 1A, and the transmitted light is measured by the associated photometer 7C. The discharge section 9 includes discharge syringes 9A, three-way valve 9B, electromagnetic valves 9C and 9D and a cleaning fluid container 9E. The control section 8 includes a LOG converter 8A which logarithmically amplifies the output of the photometry section 7, an analog/digital converter 8B, a data processing circuit 8C, a central processing unit (CPU) 8D and a drive control circuit 8E which can provide various drive control signals. The cleaning section 10 is provided for cleaning reaction tubes being fed upside down along a return path of the reaction line system 1. As the reaction tubes proceed through the cleaning section 10, their inner and outer sides are cleaned by water cleaning and then dried. The constant temperature bath 11 is provided on a part of the forward path of the reaction line system 1, in which the analysis of sample is carried out. The constant temperature bath 11 is controlled by the constant temperature control section 12 to provide a constant temperature. The constant temperature control section 12 includes a radiator 12A, heater 12B and pump 12C.

The individual sections of the automatic chemical analyzer will now be described in detail.

Figure 3:
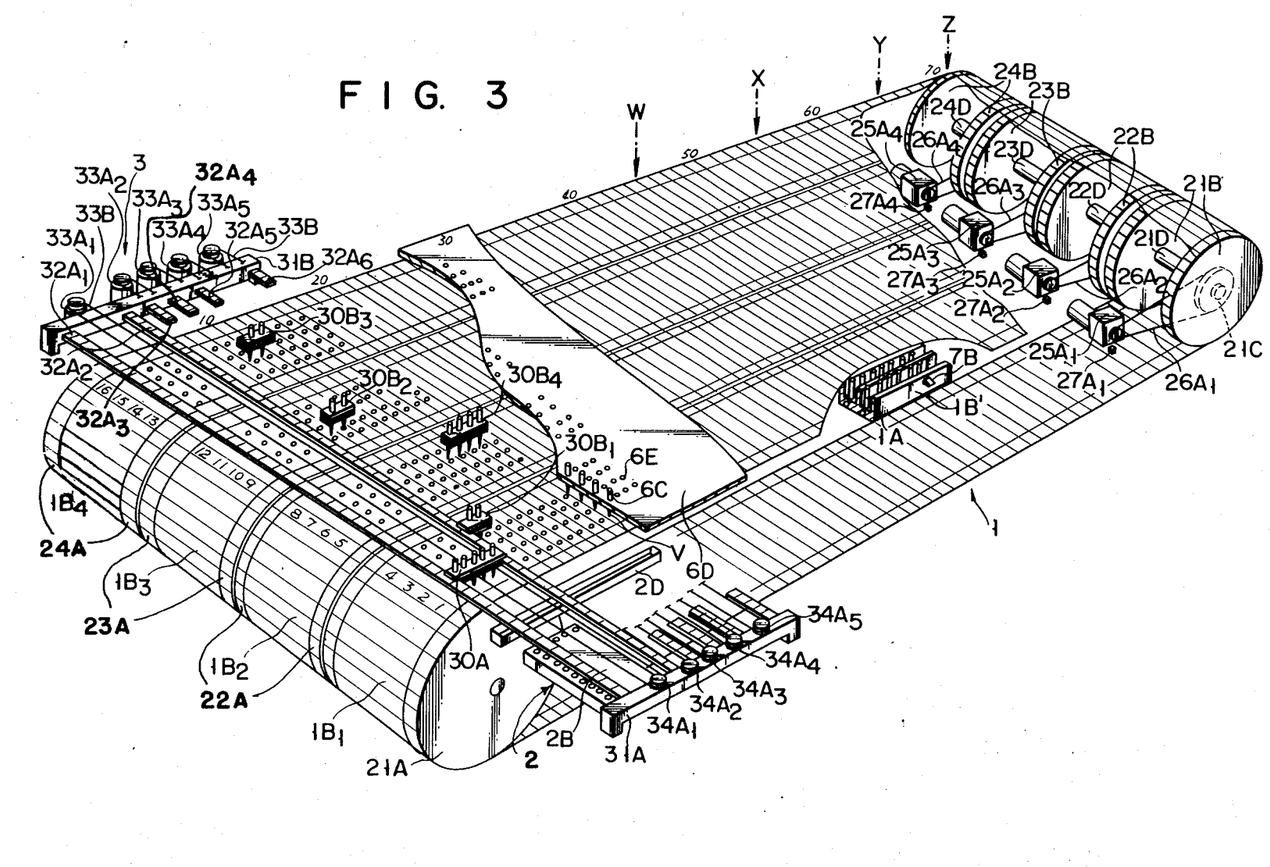
FIG. 3 is a perspective view, partly broken away, showing the reaction line system together with peripheral sections in the automatic chemical analyzer shown in FIG. 2.

First, a specific construction of the reaction line system 1 will be described with reference to FIG. 3. The reaction line system 1 includes four wide endless chain conveyors $1B_1$ to $1B_4$ disposed parallel and side by side. The individual chain conveyors are passed round respective pairs of left and right sprockets 21A and 21B, 22A and 22B, 23A and 23B and 24A and 24B. Each sprocket consists of a pair of sprocket wheels mounted on opposite ends of each of shafts 21D, 22D, 23D and 24D and spaced apart a fixed distance. The individual sprocket shafts on the right side are provided with respective timing pulleys 21C, 22C, 23C and 24C (the pulleys 22C to 23C being not shown). Near the individual right side sprockets are provided geared motors $25A_1$, $25A_2$, $25A_3$ and $25A_4$. Timing belts $26A_1$, $26A_2$, $26A_3$ and $26A_4$ are passed round the respective timing pulleys and geared motors. Near the shafts of geared motors $25A_1$ to $25A_4$ are provided respective sensors $27A_1$ to $27A_4$ to detect the rotational speed of motors.

The chain conveyors $1B_1$ to $1B_4$ are each provided with four reaction lines. The reaction line system 1 thus has a total of 16 reaction lines, which are designated by numerals 1 to 16 respectively from the end reaction line on the first chain conveyor $1B_1$. For each reaction line a reaction tube accommodating block 1B' is provided for being moved by the chain conveyor, and in which a plurality of reaction tubes are set in a row. In the apparatus of FIG. 3, 70 reaction tubes aligned as No. 1 to No. 70 reaction tubes respectively on the upper run of chain conveyor are available for each reaction line.

One feature of the automatic chemical analyzer according to the invention resides in that the four reaction lines which are provided on each of the chain conveyors $1B_1$ to $1B_4$, are independently driven as a reaction line group by the associated one of the geared motors $25A_1$ to $25A_4$. The speed of movement of each reaction line group will now be discussed.

The positions which are occupied by 70 reaction tubes in each reaction lines respectively, are referred to as positions No. 1 to No. 70 in the direction of movement. The position No. 16 is made to be a first reagent dispensing point V, the position No. 46 a first measurement point W, the position No. 56 a second measurement point X, the position No. 66 a final measurement point Y, and a position in the vicinity of the position No. 70 a discharge point Z. The longest reaction time, which is required for the relevant measurement (from the first reagent dispension till the final measurement) is assumed to be 10 minutes. In this case, the reaction tubes are moved 50 steps during the reaction time of 10 minutes since there are 50 reaction tubes between the first reagent dispensing point V, i.e., the position No. 16, and the final measurement point Y, i.e., the position No. 66, inclusive of either one of these points. One step corresponds to the center-to-center distance between adjacent reaction tubes. The time required for one step is thus 12 seconds. The reaction line for the measurement item which requires the maximum reaction time of 10 minutes, thus may be designed such that the reaction tubes are fed one step for every 12 seconds. Likewise, the reaction line for the measurement item requiring a reaction time of 5 minutes may be designed such that the reaction tubes are fed one step for every 6 seconds, and the reaction line for the measurement item requiring a reaction time of 2.5 minutes may be desinged to feed the reaction tubes one step for every 3 seconds. In the reaction line system shown in FIG. 3, the geared motors $25A_1$ to $25A_4$ for driving the respective chain conveyors $1B_1$ to $1B_4$ are adapted to provide different drive timings so that the step feed speed is 12 seconds per step for the first chain conveyor $1B_1$, 3 seconds per step for the second chain conveyor $1B_2$ and 6 seconds per step for the third and fourth chain conveyors $1B_3$ and $1B_4$. For these step feeds of chain conveyors, the geared motors $25A_1$ to $25A_4$ are driven according to motor driving signals provided from the drive control circuit 8E in the control system 8 shown in FIG. 2. The stepwise rotation of the motors is detected by the sensors $27A_1$ to $27A_4$. The reaction line group on the first chain conveyor $1B_1$ may hereinafter referred to as 10-minute line group, the reaction line group on the second chain conveyor $1B_2$ as 2.5-minute line group, and the reaction line groups on the third and fourth chain conveyors $1B_3$ and $1B_4$ as 5-minute line group.

The sampling mechanism 3 is disposed over the reaction line system 1. It includes a pair of support blocks 31A and 31B, which are disposed over the opposite sides of the feed end of the reaction line system 1 and extend parallel to the reaction lines. First to sixth guide plates $32A_1$ to $32A_6$ spaced apart at predetermined intervals extend between and are supported by the support blocks 31A and 31B. The support block 31B, which is disposed on the side of the fourth chain conveyor $1B_4$, carries five pulse motors $33A_1$ to $33A_5$ secured to its outer side. The support block 31A, which is disposed on the side of the first chain conveyor $1B_1$, carries five pulleys $34A_1$ to $34A_5$ mounted on its top at positions thereof corresponding to the pulse motors $33A_1$ to $33A_5$ respectively. A dilution nozzle holder 30A which holds five dilution nozzles strides the first and second guide plates $32A_1$ and $32A_2$ and is movable therealong. A first dispensing nozzle holder $30B_1$ which holds two dispensing nozzles strides and is movable along the second and third guide plates $32A_2$ and $32A_3$. A second dispensing nozzle holder $30B_2$ which holds two dispensing nozzles strides and is movable along the third and fourth guide plates $32A_3$ and $32A_4$. A third dispensing nozzle holder $30B_3$ which holds two dispensing nozzles strides and is movable along the fourth and fifth guide plates $32A_4$ and $32A_5$. A fourth dispensing nozzle holder $30B_4$ which holds four dispensing nozzles strides and is movable along the fifth and sixth guide plates $32A_5$ and $32A_6$. The nozzle holders 30A and $30B_1$ to $30B_4$ are mounted on respective wires 33B, which are passed round between the associated pulleys of pulse motors $33A_1$ to $33A_5$ on the support block 31A and corresponding pulleys $34A_1$ to $34A_5$ on the support block 31A. The individual nozzle holders thus can be moved along the associated guide plates by driving the pulse motors.

The sample container section 2 is disposed on the side of the first chain conveyor $1B_1$ and below the guide plates. More particularly, its sample container holder 2B is disposed between the first and second guide plates $31A_1$ and $32A_2$ and below a position which can be occupied by the dilution nozzle holder 30A. Extending between the sample container holder 2B and the first chain conveyor $1B_1$ is the cleaning pool 2D, which is elongate and has a length extending between the positions No. 1 and 15.

Returning to the description of the nozzle holders, these nozzles can cover specific alloted regions respectively. The dilution nozzle holder 30A can be moved between a position over the sample container holder 2B and a position over the reaction line No. 1. (The reaction line No. 1 thus may be hereinafter referred to as dilution line.) The first dispensing nozzle holder $30B_1$ is movable between a position over the dilution line (line No. 1) and each of positions over the reaction lines (No. 2 to No. 4) in the 10-minute line group. The second dispensing nozzle holder $30B_2$ is movable between a position over the dilution line and each of positions over the reaction lines (No. 9 to No. 12) in the first 5-minute line group. The third dispensing nozzle holder $30B_3$ is movable between the position over the dilution line and each of positions over the reaction lines (No. 13 to No. 16) in the second 5-minute line group. The fourth dispensing nozzle holder $30B_4$ is movable between the position over the dilution line and each of positions over the reaction lines (No. 5 to No. 8) in the 2.5-minute line group. It is to be noted that the individual dispensing nozzle holders are provided exclusively for the respective line groups; the first dispensing nozzle holder $30B_1$ is provided for the 10-minute line group, the second dispensing nozzle holder $30B_2$ for the first 5-minute line group, the third dispensing nozzle holder $30B_3$ for the second 5-minute line group, and the fourth dispensing nozzle holder $30B_4$ for the 2.5-minute line group. Each nozzle holder is initially located at a position over the cleaning pool 2D, and whenever it executes its task, it subsequently returns to its initial position.

Now, an example of the relation between the distance of movement of each nozzle holder and the number of nozzles held thereby will be described. Consider now a case where 300 samples are analyzed in one hour with the automatic chemical analyzer of this embodiment. In this case the treatment time per sample is 12 seconds (3,600 seconds divided by 300 samples). If it is intended to make analysis for 30 different items with respect to each sample, it is necessary to distribute sample into 30 reaction tubes in 12 seconds. In 12 seconds, the 10-minute line group is fed one step, the 5-minute line groups are fed 2 steps, and the 2.5-minute line group is fed 4 steps. To continuously supply the sample to reaction tubes, therefore, it may be supplied to a single reaction tube in the 10-minute line group, two reaction tubes in each of the 5-minute line groups and four reaction tubes in the 2.5-minute line group in 12 seconds. To this end, 5 nozzles are inserted in the dilution nozzle holder 30A, two nozzles in the first dispensing nozzle holder $30B_1$, two nozzles in each of the second and third dispensing nozzle holders $30B_2$ and $30B_3$ and four nozzles in the fourth dispensing nozzle holder $30B_4$. The dilution nozzle holder is driven for every 1-minute and each dispensing nozzle holder is driven for every 12 seconds. The supply of sample from the sampling section 2 to reaction tubes is effected by the sampling mechanism 3 and sampling control section 4 which controls the mechanism 3. In this embodiment, a quantity of sample for three or four measurements is withdrawin at a time by one nozzle, and a desired quantity of sample is supplied to each reaction tube by a dispensing syringe, which includes a pulse motor and a ball screw. Thus the same number of dispensing syringes as the dispensing nozzles are required.

The sample container holder 2B holds sample containers 2A which are arranged in five rows and 10 columns. The five dilution nozzles held in the dilution nozzle holder 30A simultaneously withdraw samples from five sample containers in a row. After the dilution nozzles have withdrawn the sample, which is not diluted, from the sample containers, they are moved to the position over the dilution line (reaction line No. 1) for charging the sample together with the diluting water (pure water) into the reaction tubes in the dilution line. To dilute the sample by five times, 300 $\mu$l of sample, for instance, is charged together with 1,200 $\mu$l of water. In this way, analysis for a number of items can be sufficiently carried out with a very small quantity of sample.

Subsequently, individual dispensing nozzles take out the diluted sample from the reaction tubes in the dilution line and distribute it to given reaction tubes in the reaction lines (No. 2 to No. 16) as will be described hereinafter.

Over the reaction lines, a plate cover 60 having a number of through holes 6E is disposed. Reagent nozzles 6C may be inserted in given through holes 6E for supplying a reagent to the reaction tubes which contain the sample. The reagent may be simultaneously supplied once for every 12 seconds at the reagent dispensing point V.

The operations of the individual sections described above, such as the driving of the chain conveyors, driving of the dilution nozzle holder and dispensing nozzle holders and distribution of samples and reagents, are all controlled according to drive control signals from the control section 8.

Now the operation of the individual sections from the sampling till the measurement will be described in detail with reference to the time charts of FIGS. 4 to 12. The positions No. 1 to No. 5 are exclusively used by the dilution nozzle holder 30A which holds five nozzles, the positions No. 6 and No. 7 are exclusively used by the first dispensing nozzle holder $30B_1$ holding two nozzles, the positions No. 8 and No. 9 are exclusively used by the second dispensing nozzle holder $30B_2$ holding two nozzles, the positions No. 10 and No. 11 are exclusively used by the third dispensing nozzle holder $30B_3$ holding two nozzles, and the positions No. 12 to No. 15 are exclusively used by the fourth dispensing nozzle holder $30B_4$ holding four nozzles. The first to fourth dispensing nozzle holders take care of their own alloted reaction lines respectively. Initially, these dispensing nozzle holders as well as the dilution nozzle holder with their nozzles are held in their stand-by positions over the cleaning pool 2D.

Figure 4:
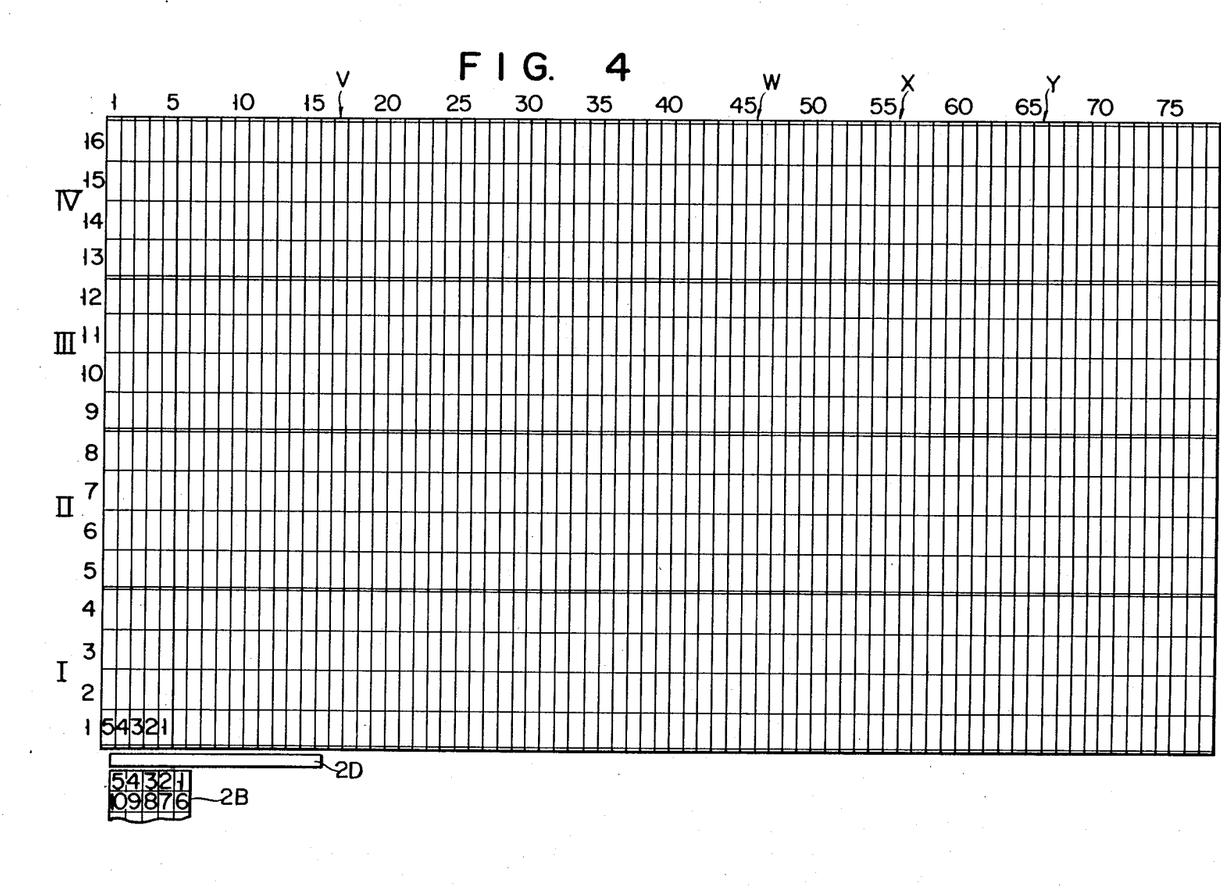
FIGS. 4 through 12 are time charts for explaining the operation of one embodiment of the automatic chemical analyzer according to the invention.

(1) Up to the 24-th second:

The five dilution nozzles held in the dilution nozzle holder 30A withdraw predetermined quantities of samples from the five sample containers (No. 1 to No. 5) in the first row in the sample container holder 2B. The dilution nozzle holder 30A is then moved to the position over the dilution line. At this position, the samples are charged together with pure water into the five reaction tubes at the position No. 1 to No. 5 in the dilution line (FIG. 4). At this time, the 10-minute line group I is being fed one step for every 12 seconds, the 5-minute line groups III and IV are being fed one step for every 6 seconds, and the 2.5-minute line group II is being fed one step for every 3 seconds.

Figure 5:
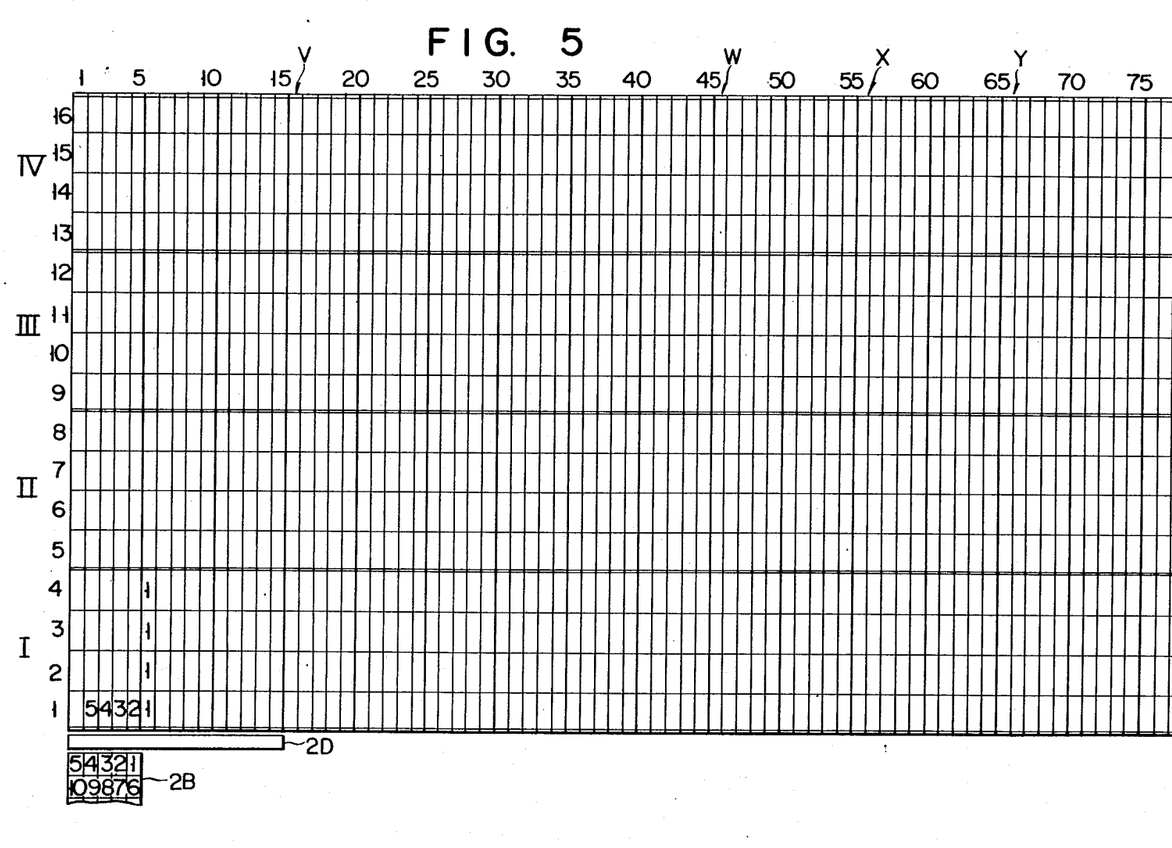

(2) From the 24-th to 36-th second:

When the 10-minute line group I has been fed one step in the 24-th through 25-th seconds, the reaction tube containing sample No. 1 is now found at the position No. 6 in the dilution line. Then the first dispensing nozzle holder $30B_1$ is moved from its set position over the cleaning pool 2D to the position over the dilution line, and the first one of the two dispensing nozzles in the nozzle holder picks up the sample No. 1 and charges it into the reaction tubes at the position No. 6 in the reaction lines No. 2 to No. 4 in the 10-minute line group successively (FIG. 5). At this time, the second nozzle at the position No. 7 is in rest for the reaction tube at the position No. 7 in the dilution line contains to sample. After the charging of sample has been completed, the first dispensing nozzle holder $30B_1$ is returned to the set position over the cleaning pool 2D, and the dispensing nozzle containing the residual sample discharges it into the cleaning pool 2D and is then cleaned there.

(3) From the 36-th to the 48-th second:

When the 10-minute line group I has been fed one step in the 36-th through 37-th seconds, the reaction tube that contains the sample No. 2 is now found at the position No. 6 in the dilution line while the reaction tubes in the reaction lines No. 2 to No. 4 that have been previously charged with the sample No. 1 comes to the position No. 7. In this state, the dispensing nozzle No. 6 (at the position No. 6), held in the first dispensing nozzle holder $30B_1$, takes out the sample No. 2 and charges it into the reaction tubes at the position No. 6 in the reaction lines No. 2 to No. 4.

Figure 6:
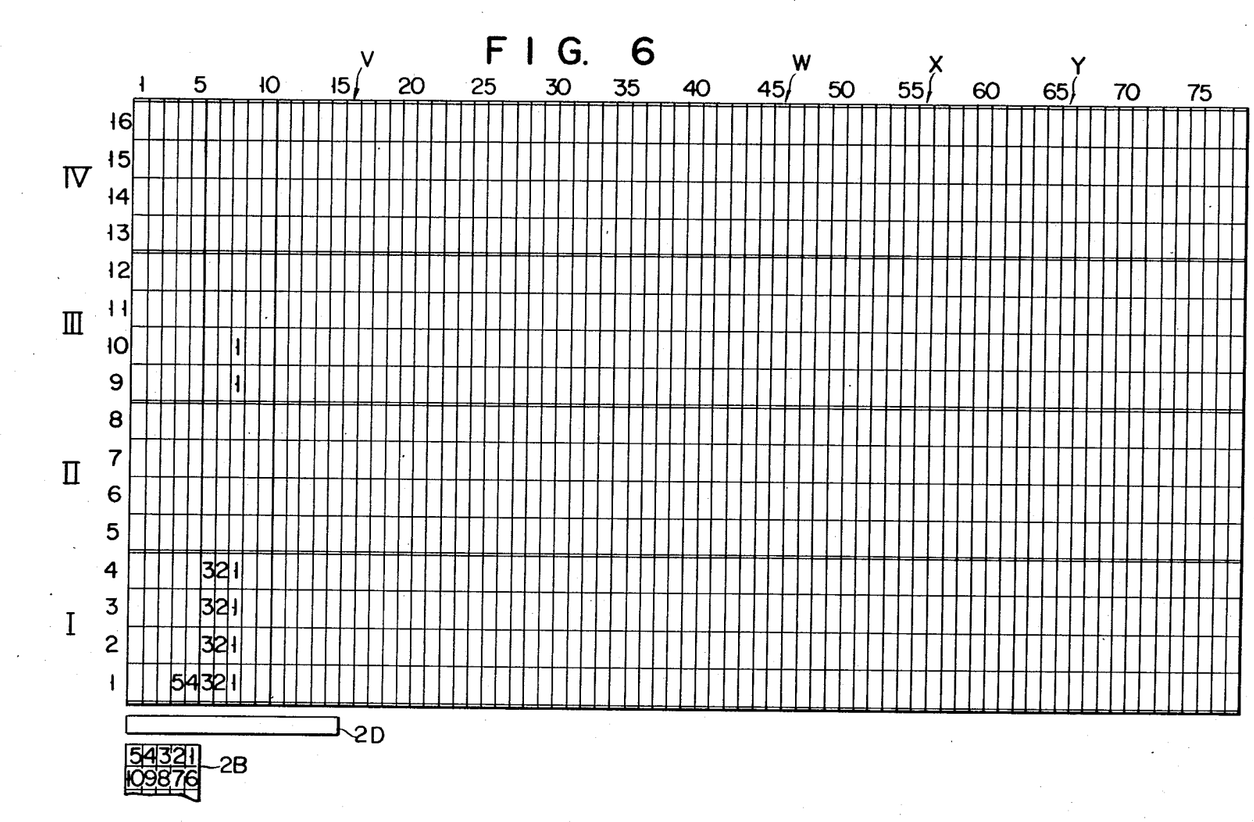

(4) From the 48-th to 54-th second:

When the 10-minute line group I has been fed a further step in the 48-th through 49-th seconds, the samples No. 1 to No. 3 that were previously at the respective positions No. 7, No. 6 and No. 5 in the dilution line are now at the positions No. 8, No. 7 and No. 6 respectively. In this state, the dispensing nozzle holder $30B_2$ which covers the positions No. 8 and No. 9 is moved from its set position over the cleaning pool 2D to the position over the dilution line, and one of the two nozzles held in the nozzle holder $30B_2$, i.e., the nozzle at the position No. 8, takes out the sample No. 1 in the reaction tube at the position No. 8 in the dilution line and charges it into the reaction tubes at the position No. 8 in the reaction lines No. 9 and No. 10 in the first 5-minute line group III. Concurrently, the nozzle at the position No. 6, held in the first dispensing nozzle holder $30B_1$, takes out the sample No. 3 at the position over the dilution line and charges it into the reaction tubes at the position No. 6 in the reaction lines No. 2 to No. 4 in the 10-minute line group (FIG. 6).

Figure 7:
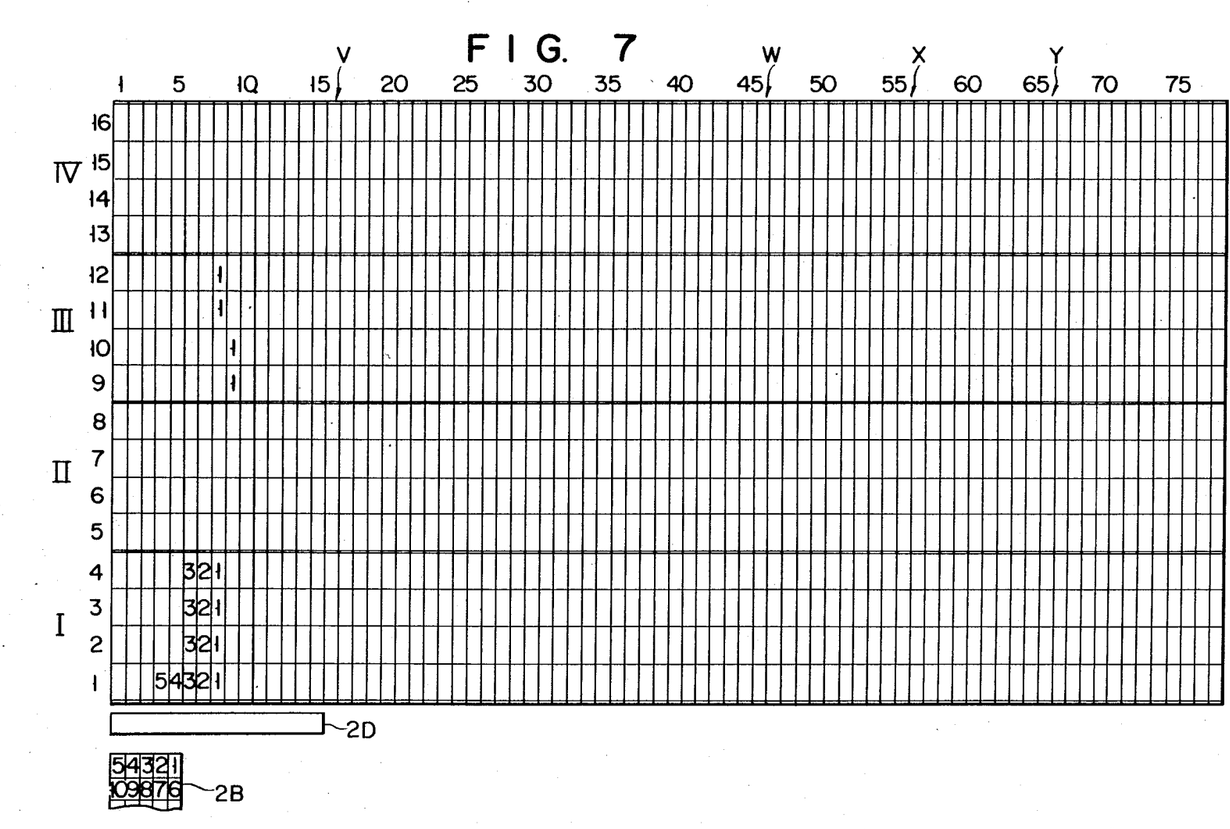

(5) From the 54-th to the 60-th second:

In the 54-th through 55-th seconds, the first 5-minute line group III is fed one step while the 10-minute line group I is not fed. In this state, the dispensing nozzle at the position No. 8 in the second dispensing nozzle holder $30B_2$, that took out the sample No. 1 in the previous period of the 48-th through 54-th seconds, charges it into the reaction tubes at the position No. 8 in the reaction lines No. 11 and No. 12 in the first 5-minute line group (FIG. 7). Subsequently the second dispensing nozzle holder $30B_2$ is returned to its set position on the cleaning pool 2D, and the dispensing nozle containing the residual sample discharges it into the cleaning pool 2D and is cleaned there.

(6) From the 60-th to the 66-th second:

In the 60-th through 61-st seconds the 10-minute line group I and first 5-minute line group III are both fed one step so that the samples No. 1 and No. 2 in the dilution line are now at the positions No. 9 and No. 8 respectively. In this state, the two nozzles held in the second dispensing nozzle holder $30B_2$ take out the respective samples No. 1 and No. 2 in the dilution line and charges them into the reaction tubes at the respective positions No. 9 and No. 8 in the reaction lines No. 9 and No. 10 in the first 5-minute line group. Meanwhile, the sample No. 4 in the dilution line is found at the position No. 6 at this time. The corresponding nozzle held in the first dispensing nozzle $30B_1$ takes out the sample No. 4 and charges it into the reaction tubes at the position No. 6 in the reaction lines No. 2 to No. 4 in the 10-minute line group. During this time, the dilution nozzle holder 30A is moved to the position over the second row of five sample containers (No. 6 to No. 10) in the sample container holder 2B, and its five dilution nozzles withdraw the samples No. 6 to No. 10 from the respective sample containers.

(7) From the 66-th to the 72-nd second:

The two nozzles in the second dispensing holder $30B_2$ that took out the samples No. 1 and No. 2 in the previous period of the 60-th to 66-th seconds, charge the samples into the four reaction tubes at the positions No. 9 and No. 8 in the reaction lines No. 11 and No. 12. During this time, the dilution nozzle holder 30A holding the dilution nozzles that took out the samples No. 6 to No. 10 from the sample containers, is moved to the position over the dilution line.

(8) From the 72-nd to the 78-th second:

In the 72-nd through the 73-rd seconds, the individual line groups are fed one step. In this state, one nozzle in the first dispensing nozzle holder $30B_1$, takes out the sample No. 5 charges it into the reaction tubes in the reaction lines No. 2 to No. 4 in the 10-minute line group. Also, two nozzles in the second dispensing nozzle holder $30B_2$ take out the samples No. 2 and No. 3 and charge them into the four reaction tubes at the positions No. 9 and No. 8 in the reaction lines No. 9 and No. 10 in the first 5-minute line group III. Further, the first one of the two nozzles in the third dispensing nozzle holder $30B_3$ takes out the sample No. 1 in the dilution line and charges it into the reaction tubes at the position No. 10 in the reaction lines No. 13 and No. 14 in the second 5-minute line group. During this time, the five dilution nozzles discharge the samples No. 6 to No. 10 into the dilution line.

Figure 8:
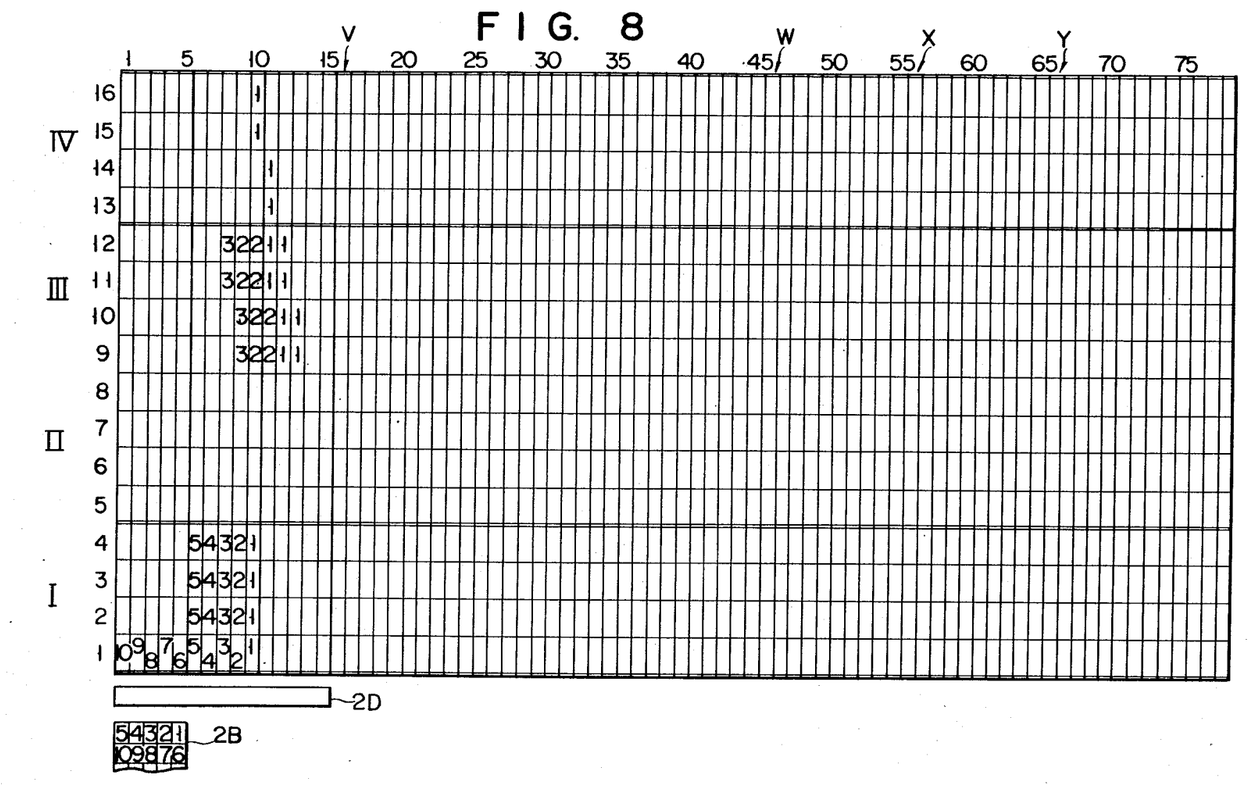
Figure 9:
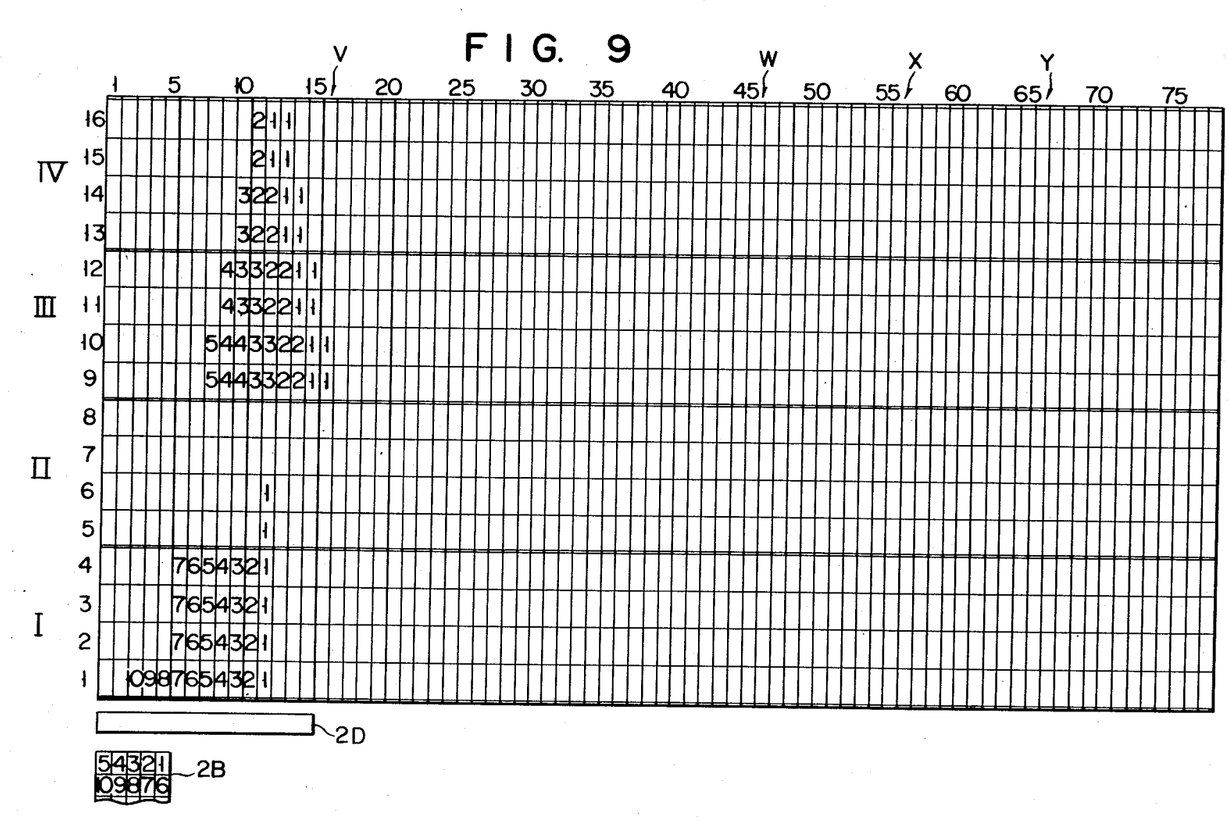

(9) From the 78-th to the 84-th second:

In the 78-th through the 79-th seconds, the 5-minute line groups III and IV are fed one step while the 10-minute line group is not fed. In this state, the two nozzles in the second dispensing nozzle holder $30B_2$ that took out the samples No. 2 and No. 3 in the previous period of the 72-nd to 78-th seconds, charge the samples into the four reaction tubes at the positions No. 9 and No. 8 in the reaction lines No. 11 and No. 12. Also, the first one of the two nozzles in the third dispensing nozzle holder $30B_3$ charges the sample No. 1 into the reaction tubes at the position No. 10 in the reaction lines No. 15 and No. 16 in the second 5-minute line group (FIG. 8).

(10) From the 84-th to the 96-th second:

In the 84-th through the 85-th seconds, the individual line groups are fed one step, and in the 90-th through 91-st seconds the 5-minute line groups III and IV are fed another step. In this state, one nozzle in the first dispensing nozzle holder $30B_1$ takes out the sample No. 6, two nozzles in the second dispensing nozzle holder $30B_2$ take out the samples No. 3 and No. 4, and two nozzles in the third dispensing nozzle holder $30B_3$ take out the samples No. 1 and No 2, and these nozzles charge the picked-up samples into the pertinent reaction tubes. During this time the dilution nozzles are brought to the position over the cleaning pool 2D and cleaned there.

(11) From the 96-th to the 102-nd second:

In the 96-th through the 97-th seconds, the individual line groups are fed one step, and in the 99-th through the 100-th seconds the 2.5-minute line group is fed another step. In this state, one nozzle in the first dispensing nozzle holder $30B_1$ distributes the sample No. 7 into the pertinent reaction tubes in the reaction lines No. 2 to No. 4 in the 10-minute line group. Also, two nozzles in the second dispensing nozzle holder $30B_2$ distribute the samples No. 4 and No. 5 into the pertinent reaction tubes in the reaction lines No. 9 and No. 10 in the first 5-minute line group. Further, two nozzles in the third dispensing nozzle holder $30B_3$ charge the samples No. 2 and No. 3 into the pertinent reaction tubes in the reaction lines No. 13 and No. 14 in the second 5-minute line group. Further, the first one of the four nozzles in the fourth dispensing nozzle holder $30B_4$ distributes the sample No. 1 into the pertinent reaction tubes in the reaction lines No. 5 and No. 6 in the 2.5-minute line group. At this time, the samples in the first 5-minute line group III are found at the first reagent dispensing point V. Thus, the first reagent is added to these samples at the point V. Subsequently, the first reagent is dispensed for every 12 seconds.

Figure 10:
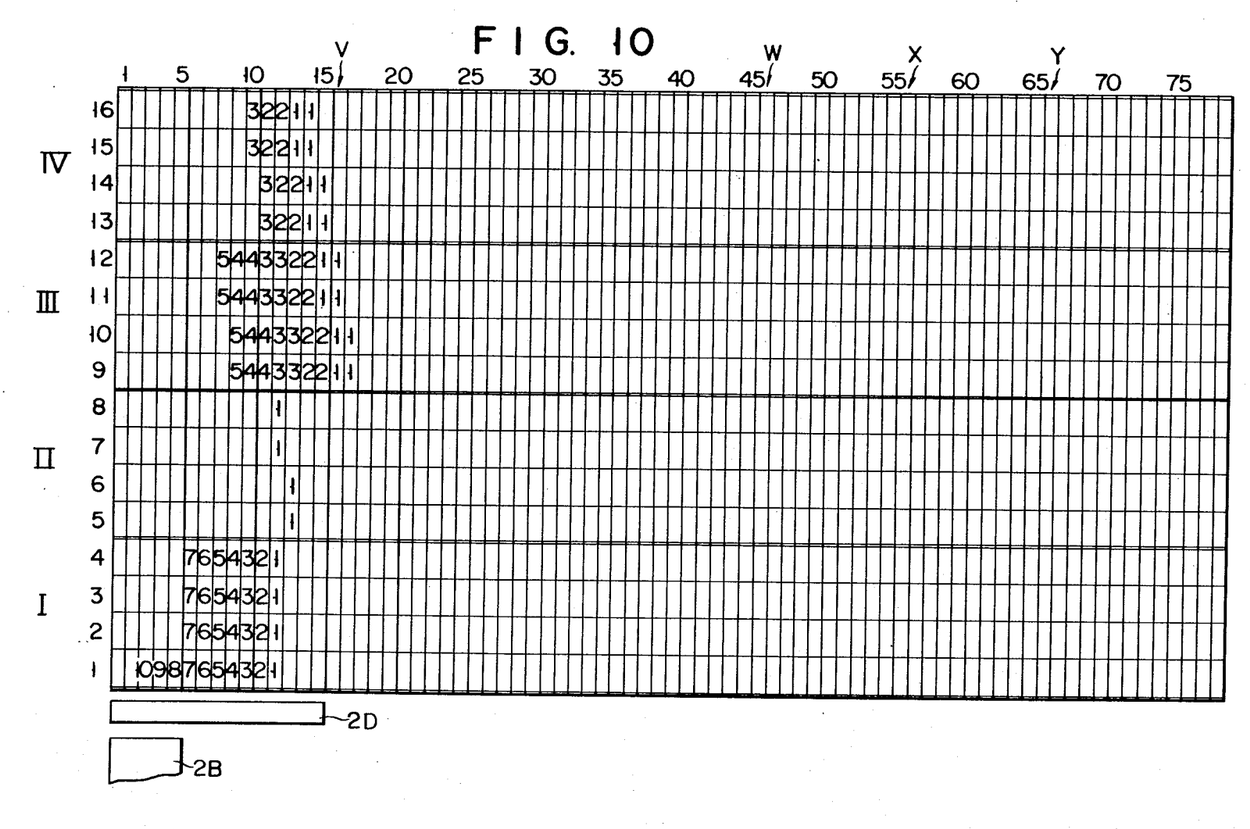

(12) From the 102-nd to the 105-th second:

In the 102-nd through the 103-rd seconds, the 5-minute line groups III and IV and 2.5-minute line group II are fed one step. The first dispensing nozzle holder $30B_1$ is brought to the position over the cleaning pool 2D. The two nozzles in the second dispensing nozzle holder $30B_2$ distribute the samples No. 4 and No. 5 to the pertinent reaction tubes in the reaction lines No. 11 and No. 12 in the first 5-minute line group. The two nozzles in the third dispensing nozzle holder $30B_3$ distribute the samples No. 2 and No. 3 to the pertinent reaction tubes in the reaction lines No. 15 and No. 16 in the second 5-minute line group IV. The first one of four nozzles in the fourth dispensing nozzle holder $30B_4$ distributes the sample No. 1 to the pertinent reaction tubes in the reaction lines No. 7 and No. 8 in the 2.5-minute line group (FIG. 10).

(13) From the 105-th to the 108-th second:

In the 105-th through the 106-th seconds, only the 2.5-minute line group II is fed one step. At this time, all the dispensing nozzles are being cleaned in the cleaning pool 2D.

(14) From the 108-th to the 111-st second:

In the 108-th through the 109-th seconds, the individual line groups are fed one step. At this time, the dispensing nozzles are withdrawing the respective samples in the dilution line.

(15) From the 111-st to the 114-th second:

In the 111-st to the 112-nd seconds, only the 2.5-minute line group is fed one step. In this state, the first one of two nozzles in the first dispensing nozzle holder $30B_1$ distributes the sample No. 8 to the reaction tubes in the reaction lines No. 2 to No. 4 in the 10-minute line group. Also, the two nozzles in the second dispensing nozzle holder $30B_2$ distribute the samples No. 5 and No. 6 to the pertinent reaction tubes in the reaction lines No. 9 and No. 10 in the first 5-minute line group. Further, the two nozzles in the third dispensing nozzle holder $30B_3$ distribute the samples No. 3 and No. 4 to the pertinent reaction tubes in the reaction lines No. 13 and No. 14 in the second 5-minute line group IV. Further, the first two of four nozzles in the fourth dispensing nozzle holder $30B_4$ distribute the samples No. 1 and No. 2 to the pertinent reaction tubes in the reaction lines No. 5 and No. 6 in the 2.5-minute line group II.

(15) From the 114-th to the 120-th second:

In the 114-th to the 115-th seconds, the 5-minute line groups III and IV and 2.5-minute line group II are fed one step. In this state, the relevant samples are distributed to the pertinent reaction tubes in the reaction lines No. 11 and No. 12, reaction lines No. 15 and No. 16 and reaction lines No. 7 and No. 8. In the subsequent 117-th to the 118-th seconds only the 2.5-minute line group II is fed one step.

(17) From the 120-th to the 132-nd second:

One of the two nozzles in the first dispensing nozzle holder $30B_1$ takes out the sample No. 9, the two nozzles in the second dispensing nozzle holder $30B_2$ take out the samples No. 6 and No. 7, the two nozzles in the third dispensing nozzle holder $30B_3$ take out the samples No. 4 and No. 5, and three of four nozzles in the fourth dispensing nozzle holder $30B_4$ distribute the samples No. 1 to No. 3 to the pertinent reaction tubes.

Figure 11:
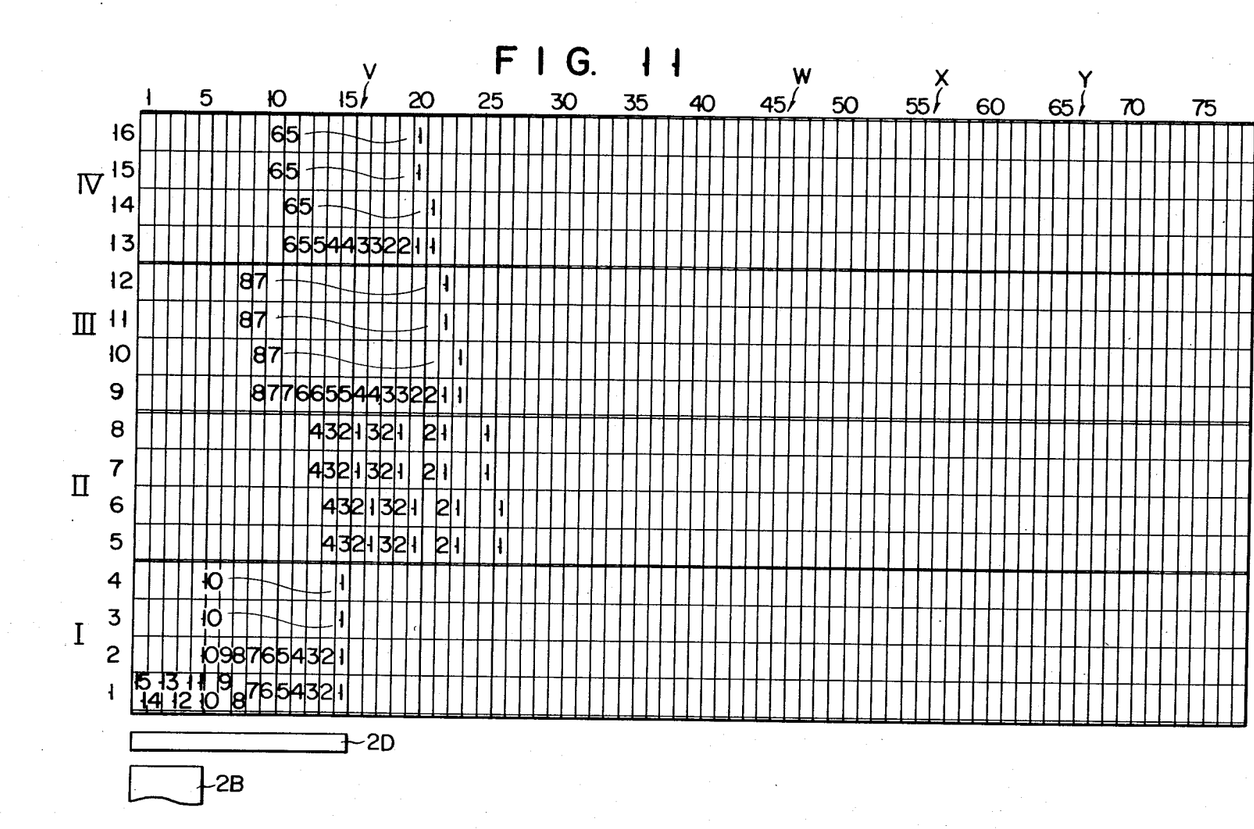

(18) From the 132-nd to the 144-th second:

One nozzle in the first dispensing nozzle holder $30B_1$ takes out the sample No. 10, the two nozzles in the second dispensing nozzle holder $30B_3$ take out the samples No. 7 and No. 8, the two nozzles in the third dispensing nozzle holder $30B_3$ take out the samples No. 5 and No. 6, and the four nozzles in the fourth dispensing nozzle holder $30B_4$ take out the samples No. 1 to No. 4. These nozzles charge the samples into the pertinent reaction tubes. During this time, the dilution nozzles discharge the samples into the reaction tubes in the dilution line (FIG. 11).

Figure 12:
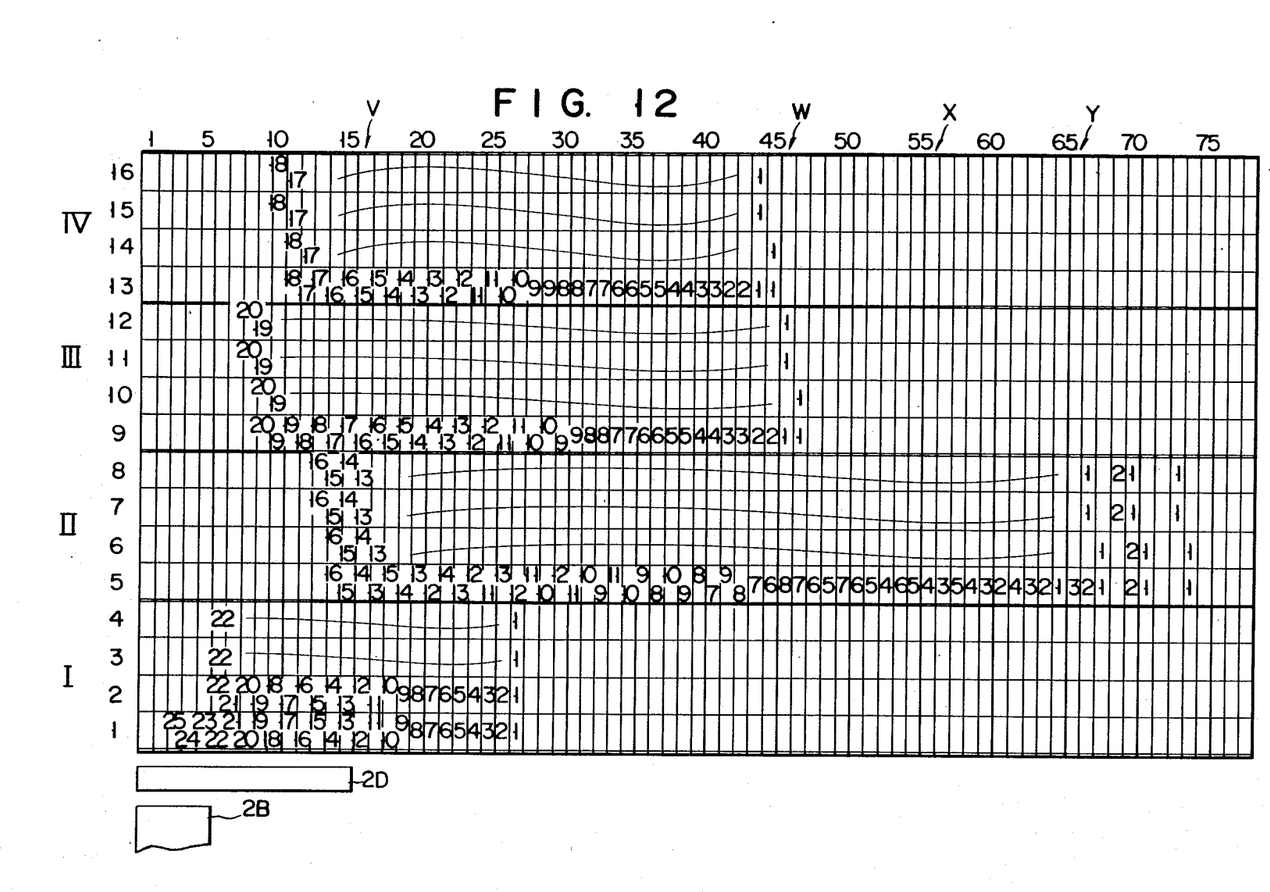

(19) From the 169-th to the 188-th second:

When the tenth cycle is ended, approximately 3 minutes has been elapsed from the start of sampling. By this time, the samples in the 2.5-minute line group have been successively brought to the final measurement point Y for measurement (FIG. 12).

Thereafter, further samples are newly distributed to the individual reaction lines and brought to the individual measurement points for measurement.

Measurements may be made in desired sequences and timings. In this embodiment, measurements are made at the three measurement points W, X and Y to see how the reaction proceeds with the lapse of time. For instance, in the 10-minute line group I the first, second and final measurements are done respectively 6, 8 and 10 minutes after the addition of the first reagent to the samples. Table 1 below shows the measurement conditions for the individual line groups.

TABLE 1

|  | First measurement | Second measurement | Final measurement |
|---|---|---|---|
| 10-minute line group | 0 to 6 minutes after adding reagent | Observation time of 4 minutes | Observation for every 2 minutes |
| 5-minute line group | 0 to 3 minutes after adding reagent | Observation time of 2 minutes | Observation for every one minute |
| 2.5-minute line group | 0 to 1.5 minutes after adding reagent | Observation time of one minute | Observation for every 0.5 minute |

The measurement is made by a direct photometric system, in which light is projected through a prism onto the sample and the absorbance is detected and converted into an electric signal by a photometer.

When the reaction tube containing the sample after the predetermined measurements reaches the discharge point Z, the sample is discharged by the action of the discharge section 9. The reaction tube is then rinsed with rinsing liquid. Thereafter, the reaction tubes are cleaned with city water and pure water and then dried in the cleaning section 10 to be ready for the next sampling operation.

With the above embodiment of the automatic chemical analyzer it is possible to make 35 different measurements for 300 samples per hour as shown in Table 2 below.

TABLE 2

| Line group | Maximum reaction time | Number of treatment items |
|---|---|---|
| Line group I | 10 minutes | 1 per line by 4 lines = 4 |
| Line group II | 2.5 minutes | 4 per line by 4 lines = 16 |
| Line group III | 5 minutes | 2 per line by 4 lines = 8 |
| Line group IV | 5 minutes | 2 per line by 4 lines = 8 |

The total number of treatment items shown in Table 2 is 36. With the above embodiment, however, the actual treatment capacity is 35 items for the reaction line No. 1 is used as the dilution line. As for the size of the reaction line system which has the treatment capacity of 35 items, one with the width dimension corresponding to 16 reaction lines and a length dimension corresponding to a row consisting of 75 reaction tubes is sufficient. Thus it is possible to obtain great size reduction compared to the prior art apparatus.

The above embodiment has been given for the purpose of illustration only, and various changes and modifications are possible. For example in the above embodiment the four reaction line groups were independently driven at the respective step feed rates of 12 seconds per step, 3 seconds per step, 6 second per step and 6 seconds per step for effecting 35 measurements, but the number of measurements may be changed by suitably changing the feed rate (reaction time) of the individual reaction line groups. Table 3 shows different examples of the line group driving to provide for different measurement capacities.

TABLE 3

| | Time (in seconds) per step (figures in parentheses representing the number of measurement items) | | | | | |
|---|---|---|---|---|---|---|
| Line group I | 12(3) | 12(3) | 12(3) | 12(3) | 6(6) | 6(6) |
| Line group II | 6(8) | 6(8) | 6(8) | 3(16) | 6(8) | 3(16) |
| Line group III | 12(4) | 6(8) | 6(8) | 6(8) | 6(8) | 6(8) |
| Line group IV | 12(4) | 12(4) | 6(8) | 6(8) | 6(8) | 6(8) |
| Total | (19) | (23) | (27) | (35) | (30) | (38) |

The feed rates of the individual line groups may be readily altered by merely changing a program stored in the CPU 8D in the control system 8.

Further, the constructions of the sampling mechanism, sampling control section and reaction line system are not limited to those in the above embodiment but can be variously modified.

As has been described in the foregoing, with the automatic chemical analyzer according to the invention, adopting a plurality of reaction lines or reaction line groups capable of being independently driven and also capable of freely altering the relative feed rates, a number of samples can be quickly and reliably treated for a number of items. In addition, it is possible to reduce the size of the apparatus more efficiently make use of the treatment time.

What we claim is:

1. An automatic chemical analyzer comprising:

a reaction line system extending along a linear reaction path and including a plurality of reaction lines each having a plurality of reaction tubes arranged in at least one row parallel to said reaction line along said reaction path and a dilution line having a plurality of dilute-sample tubes arranged in a row parallel to said dilution line along said reaction path, said dilution line and at least one of said plural reaction lines being operatively coupled so as to always move in synchrony;

driving means operatively coupled to said reaction line system for (a) driving said plural reaction lines intermittently and independently of one another at respective drive speeds such that said reaction tubes of a respective said reaction line sequentially advance through a plurality of positions along said reaction path at a different transfer rate than said reaction tubes of another of said reaction lines, and (b) driving said dilution line continually synchronously with said at least one of said plural reaction lines to which said dilution line is operatively coupled such that said dilute-sample tubes simultaneously sequentially advance through said plural positions together with said reaction tubes of said at least one reaction line;

sample holding means disposed adjacent said dilution line for holding a plurality of sample tubes containing samples to be analyzed;

dilution means for transferring predetermined ones of samples in sample tubes held by said sample holding means to respective ones of said dilute-sample tubes and for diluting samples by charging the samples together with a selected quantity of diluent into the respective ones of said dilute-sample tubes;

distributing means for distributing the diluted samples from said dilute-sample tubes of said dilution line into selected ones of said reaction tubes of said plural reaction lines;

reagent-addition means for adding at least one kind of reagent to the diluted samples in the reaction tubes in response to said drive means transferring said reaction tubes to a predetermined reagent-addition position in the respective reaction lines along said reaction path; and analyzing means for performing chemical analysis of the diluted samples in the reaction tubes in response to said drive means transferring said reaction tubes to a chemical analysis position downstream of said reagent-addition position along said reaction path.

2. The automatic chemical analyzer according to claim 1, wherein one row of one of said reaction lines comprises said dilution line.

3. The automatic chemical analyzer according to claim 1, wherein said distributing means includes at least one dispensing nozzle and means to mount said at least one dispensing nozzle for transverse reciprocal linear movements between said plural reaction lines and said dilution line.

4. The automatic chemical analyzer according to claim 3 wherein said sample holding means includes at least one fixed-position sample container disposed on a side of said dilution line.

5. The automatic chemical analyzer according to claim 4 further comprising control means for controlling said driving means to drive the plural reaction lines intermittently at said respective drive speeds.

6. The automatic chemical analyzer according to claim 5, wherein said control means includes processing unit means adapted to change the respective drive speed of a reaction line by alternating a stored program.

7. The automatic chemical analyzer according to claim 6, wherein said reaction line system includes endless chain conveyors which form said plural reaction lines and feed said reaction tubes at drive speeds determined by said controlling means.

* * * * *